US012660983B2

(12) United States Patent
Urbanski et al.

(10) Patent No.:    US 12,660,983 B2
(45) Date of Patent:        Jun. 23, 2026

(54) MEDICAL TUBULAR ASSEMBLY

(71) Applicant: Boston Scientific Medical Device Limited, Galway (IE)

(72) Inventors: John Paul Urbanski, Toronto (CA); Kaylie Lau, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 490 days.

(21) Appl. No.: 18/303,212

(22) Filed: Apr. 19, 2023

(65) Prior Publication Data

US 2023/0270316 A1      Aug. 31, 2023

Related U.S. Application Data

(63) Continuation of application No. PCT/IB2021/059566, filed on Oct. 18, 2021.

(Continued)

(51) Int. Cl.
*A61B 1/00*          (2006.01)
*A61B 1/018*        (2006.01)
*A61B 17/00*       (2006.01)

(52) U.S. Cl.
CPC .......... *A61B 1/00011* (2013.01); *A61B 1/018* (2013.01); *A61B 17/00234* (2013.01); *A61B 2017/0034* (2013.01)

(58) Field of Classification Search
CPC .... A61B 17/00234; A61B 2017/00243; A61B 5/6869; A61B 90/36; A61B 2090/3784;

(Continued)

(56) References Cited

U.S. PATENT DOCUMENTS 5,728,150 A  *  3/1998  McDonald ................ A61F 2/90
                                                                          623/1.15
10,265,100 B2    4/2019  Kassab
                          (Continued)

FOREIGN PATENT DOCUMENTS

WO              0178596 A1      10/2001
WO        2016016891 A1      2/2016

OTHER PUBLICATIONS

Extended European Search Report and Search Opinion received for European Application No. 21882271.6, mailed on Sep. 30, 2024, 7 pages.

(Continued)

*Primary Examiner* — Gerald Johnson
(74) *Attorney, Agent, or Firm* — Nelson Mullins Riley & Scarborough LLP

(57)                    ABSTRACT

An elongated medical tubular assembly is configured to improve, at least in part, transmission of a signal from the signal-transmitting device, received, at least in part, within the elongated medical tubular assembly, toward the signal-transceiving device of the medical-imaging system. The elongated medical tubular assembly defines a lumen extending from a distal tip toward a proximal end of the elongated medical tubular assembly; and the lumen is configured to receive, at least in part, the signal-transmitting device in such a way that the lumen, in use, receives, at least in part, the signal-transmitting device at the signal-liberating feature.

18 Claims, 5 Drawing Sheets

Related U.S. Application Data

(60) Provisional application No. 63/093,615, filed on Oct. 19, 2020.

(58) Field of Classification Search
CPC ... A61B 2018/0212; A61B 5/02; A61B 5/346; A61B 10/04; A61B 18/082
See application file for complete search history.

(56) References Cited

U.S. PATENT DOCUMENTS

| | | |
|---|---|---|
| 2004/0162487 A1 | 8/2004 | Klingenbeck-Regn et al. |
| 2012/0172871 A1 | 7/2012 | Hastings et al. |
| 2014/0005655 A1 | 1/2014 | Brannan |
| 2014/0121503 A1 | 5/2014 | Hamilton, Jr. |
| 2014/0275918 A1* | 9/2014 | Muse .................... A61B 5/283 600/374 |
| 2016/0007839 A1 | 1/2016 | Yoshida |
| 2018/0146948 A1* | 5/2018 | Chou .................... A61B 8/466 |
| 2020/0383750 A1* | 12/2020 | Kemp ................ A61B 1/00057 |

OTHER PUBLICATIONS

International Search Report for PCT Application No. PCT/IB2021/059566 mailed Jan. 20, 2022.

\* cited by examiner

MEDICAL TUBULAR ASSEMBLY

CROSS-REFERENCE TO RELATED APPLICATIONS

This application is a continuation of and claims the benefit of International Application Number PCT/IB 2021/059566, entitled "MEDICAL TUBULAR ASSEMBLY," and filed Oct. 18, 2021, which claims the benefit of U.S. Provisional Application No 63/093,615, entitled "MEDICAL TUBU-LAR ASSEMBLY," and filed Oct. 19, 2020, which are hereby incorporated by reference in their entireties.

TECHNICAL FIELD

This document relates to the technical field of (and is not limited to) a medical tubular assembly (and method therefor).

BACKGROUND

Known medical devices are configured to facilitate a medical procedure, and help healthcare providers diagnose and/or treat medical conditions of sick patients.

SUMMARY

It will be appreciated that there exists a need to mitigate (at least in part) at least one problem associated with known (existing) medical tubular (also called the existing technology). After much study of, and experimentation with, the known (existing) medical tubular, an understanding (at least in part) of the problem and its solution have been identified (at least in part) and are articulated (at least in part) as follows:

FIG. 1 and FIG. 2 depict cross-sectional side views of an elongated medical catheter assembly 302.

Referring to FIG. 1 and FIG. 2, the elongated medical catheter assembly 302 is configured to receive a signal-transmitting device 800. The signal-transmitting device 800 may be positioned or mounted to (onto) the distal section of, for instance, an elongated medical needle 802, etc. For instance, the signal-transmitting device 800 may include, preferably, a material that facilitates transmission of the signal (such as a metal for current, a sensor, a distal energy-emitting device configured to selectively emit energy (such as, radiofrequency energy)) toward a biological feature of a patient 700, for forming a puncture through (or cutting a portion of) a biological feature of the patient 700, etc., during a medical procedure.

Referring to FIG. 1 and FIG. 2, a medical-imaging system 902 is configured to generate (compute, determine, etc.) a medical image of the patient 700 and the signal-transmitting device 800. The medical-imaging system 902 is also configured to display the medical images (that were generated or computed) on a medical display device (known and not depicted) to a physician during a medical procedure, such as a transseptal procedure (a procedure may be performed by a cardiac electrophysiologist, etc.). The transseptal procedure may include forming a transseptal puncture to access the left atrium of the heart of the patient 700, predominantly for ablation of atrial fibrillation. For the case where the medical-imaging system 902 may include, for instance, a fluoroscopy system (configured to emit radiation energy therefrom), there may be an adverse risk posed to the patient and/or the physician associated with continued use of fluoroscopy (that is, the emission of too much radiation) during the transseptal procedure.

Referring to FIG. 1 and FIG. 2, for instance, adapting the elongated medical catheter assembly 302 may lead to the usage of a different type medical-imaging systems (potential alternatives to fluoroscopy, etc.) for the medical-imaging system 902, such as (and not limited to) echocardiography, an electro-anatomical mapping (EAM) system, etc. (which may not require the emission of radiation). This case may provide an opportunity to reduce (preferably, eliminate) the need for fluoroscopy (which involves the emission of radiation), thereby reducing unwanted exposure to excessive radiation (which might be associated with, or emitted from, a certain type of the medical-imaging system 902 such as a fluoroscopy system, etc.) while the medical catheter assembly 302 is positioned within the patient 700 (such as, within the heart of the patient 700). For instance, it may be desirable to have the elongated medical needle 802 be detected by an electro-anatomical mapping system (a type of medical-imaging system 902) either prior to performing, while performing or after performing the transseptal puncture on the patient 700 (that way, the aforementioned radiation risk may be averted). For this case, the physician may visualize (via the display unit of the electro-anatomical mapping system) the signal-transmitting device 800 as a representative medical image (such as, a dot, a point, a spot image) formed within (positioned within) a three dimensionally-generated volume (another medical image) representing the biological feature (such as, the right artery of the heart) of the patient 700.

Referring to FIG. 1 and FIG. 2, unfortunately, the location of the signal-transmitting device 800 might be displayed on the visual display unit (the medical image may become inadvertently lost or hidden, or might not remain depicted in the visual display unit) after the signal-transmitting device 800 has been retracted into an interior of the medical catheter assembly 302. For this case, the medical catheter assembly 302 inadvertently hides (shelters, blocks) the signal communication from (between) the signal-transmitting device 800 to (and) the signal-transceiving device 900 of the medical-imaging system 902. This unfortunate case may prevent, or interfere with, the formation of a desirable medical image on the visual display unit of the medical-imaging system 902 (that is, while the signal-transmitting device 800 is received within the medical catheter assembly 302). The medical catheter assembly 302 is configured to provide a layer of signal insulation (signal-blocking material) positioned over the signal-transmitting device 800 positioned within the interior of the medical catheter assembly 302. For instance, the signal-transmitting device 800 may need to remain inside of the medical catheter assembly 302 during a drop-down portion of a medical procedure (such as, when pulling the medical catheter assembly 302 from the superior vena cava (SVC) to the atrial septum of the heart of the patient 700, etc.). Unfortunately, the medical procedure is performed (by the physician) blind; the visual display unit (of the medical-imaging system 902) cannot, unfortunately, provide, to the physician, a suitable medical image of the signal-transmitting device 800. Specifically, the medical-imaging system 902 may become blind (unable to detect the presence of the signal-transmitting device 800) to the movements of the signal-transmitting device 800 along (and within) the interior of the medical catheter assembly 302. Moreover, the medical-imaging system 902 may not be able to provide an adequate visual display of the medical image of the movements of the signal-transmitting device

800 for the case where the signal-transmitting device 800 may be slightly extended along the lumen 108 forwardly away from the exit portal of the distal tip 104 of the medical catheter assembly 302; it will be appreciated that this may become a rather sensitive situation for the physician (that is, to operate undesirably under blind conditions, and potentially inflict inadvertent (unwanted) injury to the patient 700). It will be appreciated that for the embodiment of FIG. 1, the signal-transceiving device 900 is able to properly (reliably) receive the signal from the signal-transmitting device 800. It will be appreciated that for the embodiment of FIG. 2, the signal-transceiving device 900 is not able to properly (not able to reliably) receive the signal from the signal-transmitting device 800.

Referring to the embodiment (implementation) as depicted in FIG. 1, the signal-transmitting device 800 has been extended from the exit portal of the medical dilator assembly 302 to such an extent that the signal-transceiving device 900 (of the medical-imaging system 902) is able to adequately detect the presence of the signal-transmitting device 800 and generate a suitable medical image thereof. For signal triangulation (that is, to determine the location of a signal source), the signal-transceiving device 900 may include (at least a quantity of three) spaced-apart signal-transceivers (901A, 901B, 901C), such as a series of at least three surface electrodes (or devices or material which can transmit or receive electrical signal) configured to be placed on a surface of the patient 700 (such as, on the chest of the patient 700, etc.).

Referring to the embodiment (implementation) as depicted in FIG. 2, the signal-transmitting devices 800 has been moved along (extended into or retracted from) the interior of the medical dilator assembly 302 to such an extent that the signal-transceiving device 900 is now unable to (a) reliably detect the presence (location) of the signal-transmitting device 800 and (b) generate a medical image since detection is not possible. For instance, the spaced-apart signal-transceivers (901A, 901B, 901C) are unable to successfully triangulate a reliable signal and is unable to reliably determine the location of a signal. Successful triangulation requires all of the spaced-apart signal-transceivers (901A, 901B, 901C) to receive an incoming signal from the signal-transmitting device 800. Unsuccessful triangulation results when less than a quantity of three spaced-apart signal-transceivers (901A, 901B, 901C), in use, fail to receive any incoming signal from the signal-transmitting device 800. For this case, the medical-imaging system 902 is not able to provide any adequate visual display of the medical image of the movements of the signal-transmitting device 800 while the signal-transmitting device 800 remains within the lumen 108 and rearward from the distal tip 104 of the medical catheter assembly 302. It will be appreciated that this may become a rather sensitive situation for the physician (to operate undesirably blind may cause inadvertent injury to the patient 700).

Referring to FIG. 1 and FIG. 2, in view of the above description, what may be desirable (to improve safety and/or positioning accuracy of the signal-transmitting device 800 during a portion of a medical procedure (such as, the transseptal puncture procedure), thereby providing, at least in part, a technical solution to assist in the visualization (via the medical-imaging system 900) of a suitable medical image of the signal-transmitting device 800 while the signal-transmitting device 800 is positioned or located inside of the medical catheter assembly 302 (preferably, at all times or at least most of the time).

To mitigate, at least in part, at least one problem associated with the existing technology, there is provided (in accordance with a major aspect) an apparatus. The apparatus is for use with a patient, a signal-transmitting device and a signal-transceiving device of a medical-imaging system. The apparatus includes and is not limited to (comprises) an elongated medical tubular assembly having a distal tip configured to be received in the patient. The elongated medical tubular assembly is configured to receive the signal-transmitting device at the distal tip. The distal tip is configured to improve, at least in part, transmission of a signal from the signal-transmitting device toward the signal-transceiving device of the medical-imaging system.

To mitigate, at least in part, at least one problem associated with the existing technology, there is provided (in accordance with a major aspect) an apparatus. The apparatus is for use with a patient, a signal-transmitting device and a signal-transceiving device of a medical-imaging system. The apparatus includes and is not limited to (comprises) an elongated medical tubular assembly configured to be received in the patient. The elongated medical tubular assembly includes a signal-liberating feature configured to improve, at least in part, transmission of a signal from the signal-transmitting device, positioned in an interior of the elongated medical tubular assembly, toward the signal-transceiving device of the medical-imaging system.

To mitigate, at least in part, at least one problem associated with the existing technology, there is provided (in accordance with a major aspect) a method. The method is for enhancing transmission of a signal from a signal-transmitting device toward a signal-transceiving device of a medical-imaging system while the signal-transmitting device is positioned in a patient. The method includes and is not limited to (comprises) receiving an elongated medical tubular assembly having a distal tip into the patient. The method also includes receiving the signal-transmitting device at the distal tip of the elongated medical tubular assembly. The distal tip is configured to improve, at least in part, transmission of a signal from the signal-transmitting device toward the signal-transceiving device of the medical-imaging system.

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

Figure 1:
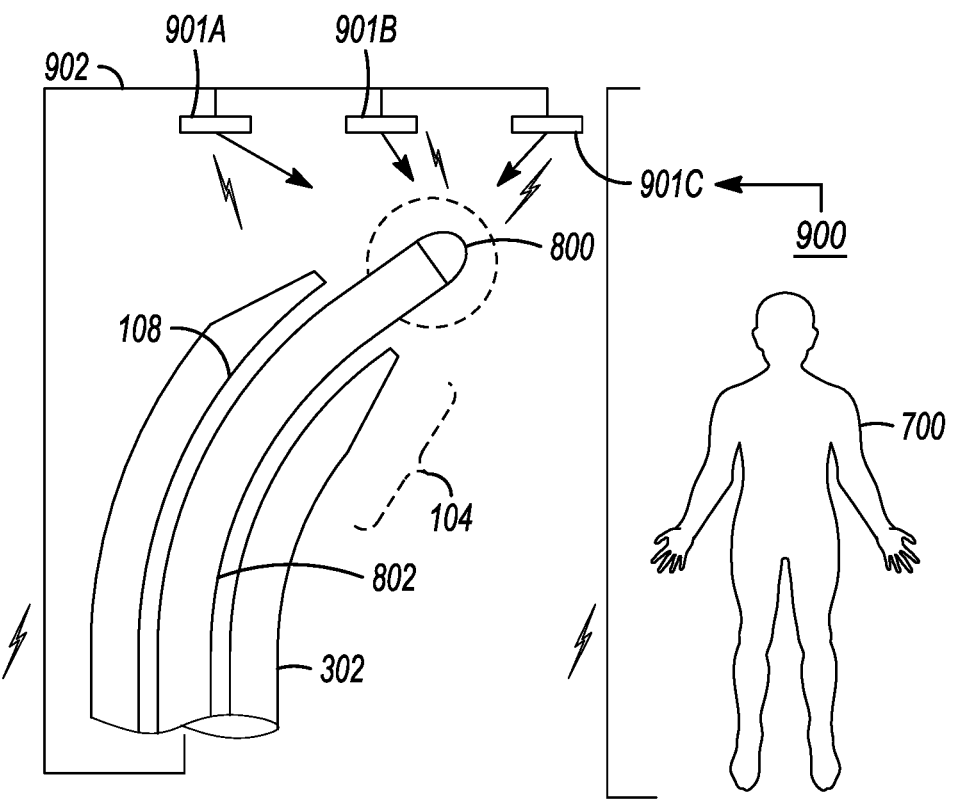
FIG. 1 and FIG. 2 depict cross-sectional side views of an elongated medical catheter assembly.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are useful in commercially feasible embodiments are often not

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the disclosure is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the disclosure is limited to the subject matter provided by the claims, and that the disclosure is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, "configured to" may include the meaning "either directly or indirectly" unless specifically stated otherwise.

Figure 3:
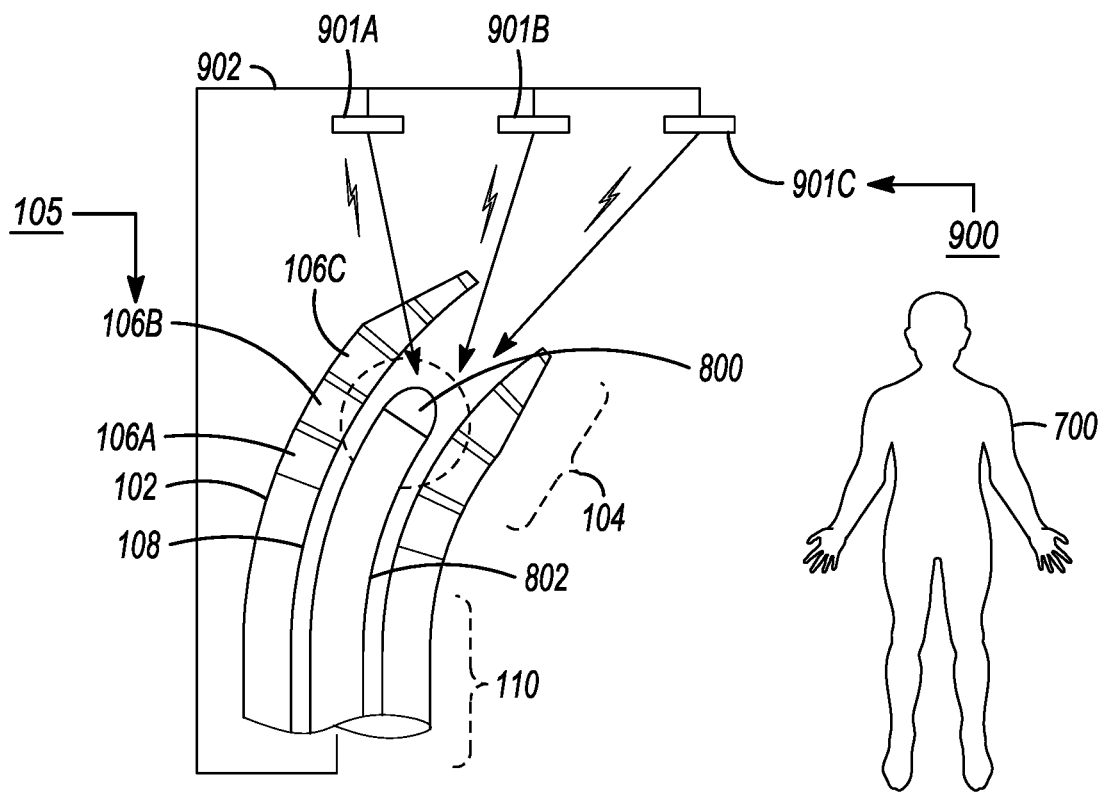
FIG. 3 and FIG. 4 depict a cross-sectional view (FIG. 3) and a side view (FIG. 4) of embodiments (implementations) of an elongated medical tubular assembly.
Figure 4:
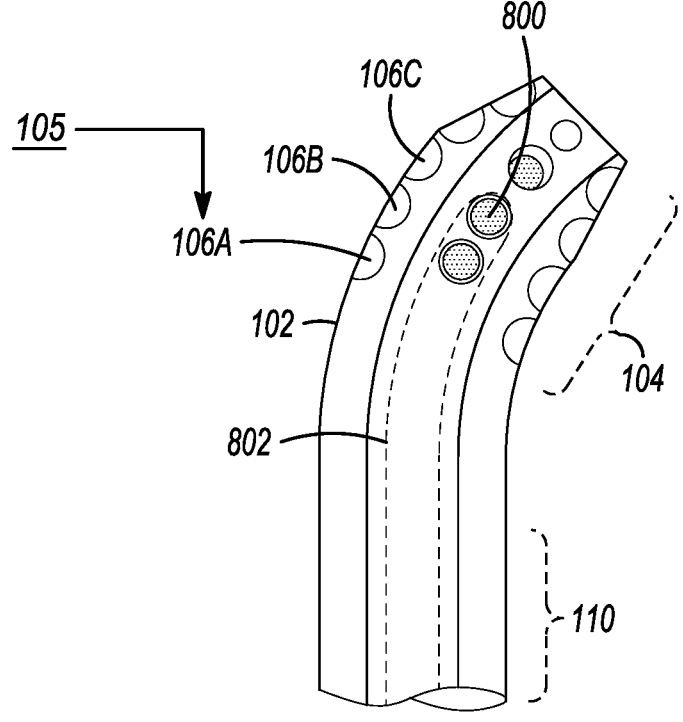

FIG. 3 and FIG. 4 depict a cross-sectional view (FIG. 3) and a side view (FIG. 4) of embodiments (implementations) of an elongated medical tubular assembly 102.

Figure 2:
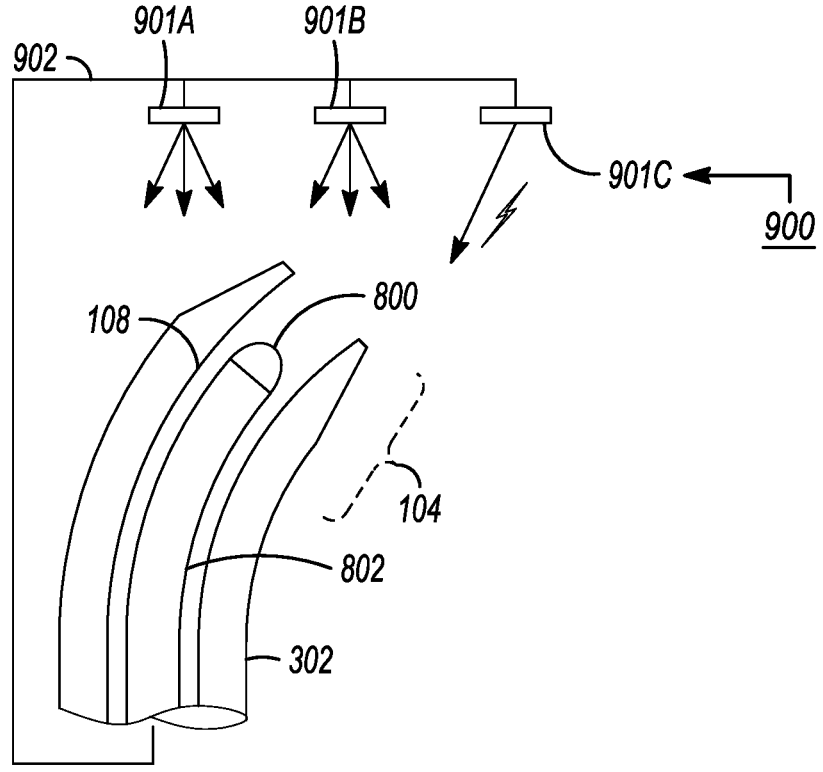

Referring to the embodiment (implementation) as depicted in FIG. 3, the elongated medical tubular assembly 102 is configured for use with a patient 700, a signal-transmitting device 800 and a signal-transceiving device 900 of a medical-imaging system 902. The signal-transmitting device 800 may be, preferably, installed or mounted to (onto) an elongated medical needle 802. The elongated medical needle 802 is configured to be received (at least in part) into the patient 700. The signal-transmitting device 800 may be, preferably, installed or mounted to (onto) a distal tip 104 of the elongated medical needle 802, in which case the signal-transmitting device 800 includes an energy emitter (electrode or material which can transmit or receive electrical signal) configured to selectively emit energy (preferably, radiofrequency energy) toward a biological feature of the patient 700. The emission of energy (from the signal-transmitting device 800) is used for forming a puncture through (or cutting a portion of) a biological feature of the patient 700, etc., during a medical procedure. It will be appreciated that for the embodiment of FIG. 3, the signal-transceiving device 900 is able to properly (reliably) receive the signal from the signal-transmitting device 800 (in sharp contrast to the embodiment as depicted in FIG. 2).

Referring to the embodiment (implementation) as depicted in FIG. 3, the signal-transmitting device 800 may include (and is not limited to) a radiofrequency puncture device of the BAYLIS (TRADEMARK) NRG (REGISTERED TRADEMARK) Transseptal Needle manufactured by BAYLIS MEDICAL COMPANY (headquartered in Canada).

Referring to the embodiment (implementation) as depicted in FIG. 3, the elongated medical tubular assembly 102 includes, preferably, biocompatible material properties suitable for specific performance (such as, dielectric strength, thermal, electrical insulation, corrosion, water resistance, heat resistance, etc.) for compliance with industrial and regulatory safety standards (or compatible for medical usage), etc. Reference is made to the following publication for consideration in the selection of a suitable material: Plastics in Medical Devices: Properties, Requirements, and Applications; 2nd Edition; author: Vinny R. Sastri; hardcover ISBN: 9781455732012; published: 21 Nov. 2013; publisher: Amsterdam [Pays-Bas]: Elsevier/William Andrew, [2014].

Referring to the embodiment (implementation) as depicted in FIG. 3, the elongated medical tubular assembly 102 and/or the elongated medical needle 802 may, if so desired, include a shape-memory material configured to be manipulated and/or deformed followed by a return to the original shape that the shape-memory material was set in (prior to manipulation). Shape-memory materials (SMMs) are known and not further described in detail. Shape-memory materials are configured to recover their original shape from a significant and seemingly plastic deformation in response to a particular stimulus being applied to the shape-memory material. This is known as the shape memory effect (SME). Superelasticity (in alloys) may be observed once the shape-memory material is deformed under the presence (an application) of a stimulus force.

Referring to the embodiment (implementation) as depicted in FIG. 3, the elongated medical tubular assembly 102 is configured to be received, at least in part, into the patient 700. The elongated medical tubular assembly 102 is also configured to receive the signal-transmitting device 800. The elongated medical tubular assembly 102 is, preferably, also configured to receive the elongated medical needle 802 with the signal-transmitting device 800 mounted thereto. The elongated medical tubular assembly 102 may include, for instance, any type of elongated medical tube, medical catheter assembly, a medical dilator assembly, a medical sheath assembly, etc., and/or any equivalent thereof. The elongated medical tubular assembly 102 has, preferably, a distal tip 104 configured to be received in the patient 700. The elongated medical tubular assembly 102 is configured to receive the signal-transmitting device 800 at the distal tip 104. The elongated medical tubular assembly 102 is (preferably) configured to be received within the interior of the elongated medical tubular assembly 102 such as a lumen 108 so that the signal-transmitting device 800 may be positioned, or movable, at the distal tip 104.

Referring to the embodiment (implementation) as depicted in FIG. 3, the distal tip 104 is configured to improve (facilitate, promote), at least in part, transmission of a signal (signal communication) from the signal-transmitting device 800 toward the signal-transceiving device 900 (such as electrode or material which can transmit or receive electrical signal) of the medical-imaging system 902. Preferably, the distal tip 104 is configured to improve, at least in part, transmission of the signal (signal communication) between the signal-transmitting device 800 and the signal-transceiving device 900 of the medical-imaging system 902.

Referring to the embodiment (implementation) as depicted in FIG. 3, the elongated medical tubular assembly 102 defines (preferably) a lumen 108 extending from the distal tip 104 toward a proximal end 110 of the elongated medical tubular assembly 102. The lumen 108 is configured to receive the signal-transmitting device 800 at the proximal end 110. The lumen 108 is configured to guide movement (limit movement) of the signal-transmitting device 800 from the proximal end 110 toward the distal tip 104 (along a forward movement). The lumen 108 is configured to guide movement (limit movement) of the signal-transmitting device 800 back to the proximal end 110 from the distal tip 104 (along a rearward movement).

Referring to the embodiment (implementation) as depicted in FIG. 3, the elongated medical tubular assembly 102 defines spaced-apart perforations (106A, 106B, 106C). The spaced-apart perforations (106A, 106B, 106C) extend from the interior of the elongated medical tubular assembly 102 to the exterior of the elongated medical tubular assembly 102. The spaced-apart perforations (106A, 106B, 106C) are configured to provide fluid communication between the interior of the elongated medical tubular assembly 102 and the exterior of the elongated medical tubular assembly 102. The distal tip 104, preferably, defines the spaced-apart perforations (106A, 106B, 106C). The spaced-apart perforations (106A, 106B, 106C) are a preferred embodiment of a signal-liberating feature 105. Generally, the elongated medical tubular assembly 102 includes the signal-liberating feature 105. The signal-liberating feature 105 may include, and is not limited to, the spaced-apart perforations (106A, 106B, 106C), and any equivalent thereof. It will be appreciated that other embodiments of the signal-liberating feature 105 are described below. The signal-liberating feature 105 is mounted to, or located with, the elongated medical tubular assembly 102. The signal-liberating feature 105 is, preferably, mounted to, or located at, the distal tip 104 of the elongated medical tubular assembly 102. The signal-liberating feature 105 is configured to promote, or foster the connection of, signal communication (signal transmission) between the signal-transmitting device 800 and the signal-transceiving device 900 of the medical-imaging system 902. The signal-liberating feature 105 is configured to improve (not block), at least in part, transmission of a signal (signal communication) from (between) the signal-transmitting device 800 toward (and) the signal-transceiving device 900 of the medical-imaging system 902 while the signal-transmitting device 800 remains positioned in (or moves therealong) the elongated medical tubular assembly 102. Signal transmission may include unidirectional signal transmission and/or bidirectional signal transmission (either direct and/or indirect signal transmission).

Referring to the embodiment (implementation) as depicted in FIG. 3, the lumen 108 is configured to receive the signal-transmitting device 800; this is done, preferably, in such a way that the lumen 108, in use, guides movement of the signal-transmitting device 800 toward the spaced-apart perforations (106A, 106B, 106C) positioned at the distal tip 104. The spaced-apart perforations (106A, 106B, 106C) are configured to improve (not block), at least in part, transmission of a signal (signal communication) from (between) the signal-transmitting device 800 toward (and) the signal-transceiving device 900 of the medical-imaging system 902 while the signal-transmitting device 800 remains positioned in (or moves therealong) the lumen 108 at, or proximate to, the spaced-apart perforations (106A, 106B, 106C).

Referring to the embodiment (implementation) as depicted in FIG. 3, there is depicted a method for enhancing transmission of a signal from the signal-transmitting device 800 toward the signal-transceiving device 900 (of the medical-imaging system 902) while the signal-transmitting device 800 is positioned in the patient 700. The method includes receiving the elongated medical tubular assembly 102 having the distal tip 104 into the patient 700. The method also includes receiving (locating, positioning or moving) the signal-transmitting device 800 at the distal tip 104 (of the elongated medical tubular assembly 102); the distal tip 104 is configured to improve, at least in part, transmission of a signal (signal communication) from (between) the signal-transmitting device 800 toward (and) the signal-transceiving device 900 of the medical-imaging system 902.

Referring to the embodiment (implementation) as depicted in FIG. 3, there is depicted a method for enhancing transmission of a signal from (between) the signal-transmitting device 800 toward (and) the signal-transceiving device 900 (of the medical-imaging system 902) while the signal-transmitting device 800 is located within the elongated medical tubular assembly 102. The method includes receiving the distal tip 104 of the elongated medical tubular assembly 102 into the patient 700. The distal tip 104 defines spaced-apart perforations (106A, 106B, 106C), or provides the signal-liberating feature 105. The elongated medical tubular assembly 102 defines the lumen 108 extending between the distal tip 104 and the proximal end 110 of the elongated medical dilator assembly 110. The lumen 108 is configured to receive the signal-transmitting device 800; this is done, preferably, in such a way that the lumen 108, in use, receives the signal-transmitting device 800 at the spaced-apart perforations (106A, 106B, 106C), or at the signal-liberating feature 105. The method also includes using the signal-liberating feature 105, or the spaced-apart perforations (106A, 106B, 106C), to improve, at least in part, signal transmission of the signal between (from) the signal-transmitting device 800, positioned in the lumen 108, and (toward) the signal-transceiving device 900 of the medical-imaging system 902.

Referring to the embodiment (implementation) as depicted in FIG. 3, the elongated medical tubular assembly 102 has a side wall body member configured to permit transmission of a signal (communication signal) from (between) the signal-transmitting device 800 to (and) the medical-imaging system 902 (or between the signal-transmitting device 800 and the medical-imaging system 902). In sharp contrast to the catheter assembly 302 (as depicted in FIG. 1 and FIG. 2), the catheter assembly 302 has a body configured to block (insulate, prevent, retard, attenuate) the transmission of signal communication from (between) the signal-transmitting device 800 to (and) the medical-imaging system 902. The medical-imaging system 902 is configured to be in electrical communication (either wirelessly or wired) with the signal-transceiving device 900.

Referring to the embodiment (implementation) as depicted in FIG. 3, the medical-imaging system 902 is configured to communicate (via the signal-transceiving device 900) a communication signal (electrically, either wired or wirelessly) with the signal-transmitting device 800 (such as, an energy emitter, or electrode, of a medical needle) positioned inside the catheter assembly 102 (while the catheter assembly 102 is positioned in the patient 700). The medical-imaging system 902 may include an electro-anatomical mapping system, fluoroscopy system, or any equivalent thereof, etc.). According to a preferred embodiment, in which it may be desired to avoid radiation altogether, the medical-imaging system 902 may exclude the fluoroscopy system in order to avoid any unwanted exposure to radiation to the patient and/or the physician, etc. The medical-imaging system 902 is configured to locate a spatial position of the signal-transmitting device 800 positioned inside the patient 700 (via cooperative action with the signal-transceiving device 900). For instance, the medical-imaging system 902 may utilize a triangulation method (known and not described herein), or arrangement, configured to make a determination of the spatial position of the signal-transmitting device 800. The triangulation method or arrangement may include placing the signal-transceiving device 900 on a surface of the patient 700 (such as, on the chest of the patient 700). More specifically, for triangulation of the signal provided by the signal-transmitting device 800, the signal-transceiving device 900 may include (at least a quantity of three) signal-transceivers (901A, 901B, 901C), such as a series of at least three surface electrodes configured to be placed on a surface of the patient 700 (such as, on the chest of the patient 700). When the signal-transmitting device 800 (energy emitter or electrode) is placed inside of the elongated medical tubular assembly 102, the elongated medical tubular assembly 102 has a sidewall member or position configured to promote (enhance) signal transmission of signal communication from (between) the signal-transmitting device 800 to (and) the medical-imaging system 902 via (the signal-transceiving device 900). The elongated medical tubular assembly 102 has at least one side wall portion configured to avoid, at least in part, the entire blockage (signal insulation) of the transmission of any signal communication from (between) the signal-transmitting device 800 to (and) the medical-imaging system 902 via (the signal-transceiving device 900). For this case, visualization (or "triangulation") of the signal-transmitting device 800 is improved, at least in part, by the catheter assembly 102 (in sharp contrast to the embodiment as depicted in FIG. 1 and FIG. 2). Visualization of the signal-transmitting device 800 (by the medical-imaging system 902) may be improved by modifying, at least in part, a section of the catheter assembly 102, such as a distal tip 104 of the catheter assembly 102.

Referring to the embodiment (implementation) as depicted in FIG. 3, for instance, in accordance with a first option, the signal-liberating feature 105 may include the spaced-apart perforations (106A, 106B, 106C), or windows, positioned or placed at a section (such as, at the distal tip 104) of the elongated medical tubular assembly 102; this arrangement may allow for improved signal communication between the signal-transceiving device 900 (also called surface electrodes) and the signal-transmitting device 800 (such as a puncture device of a medical needle assembly, etc.). The spaced-apart perforations (106A, 106B, 106C) are configured to not adversely interact with the tissue of the patient 700, supported devices, etc.

Referring to the embodiment (implementation) as depicted in FIG. 3, for instance, in accordance with a second option, the signal-liberating feature 105 (of the elongated medical tubular assembly 102) may include (at least in part) signal-enhancing material surrounded by the signal-blocking material of the elongated medical tubular assembly 102; this arrangement may allow for improved signal communication between the signal-transceiving device 900 (also called surface electrodes) and the signal-transmitting device 800 (such as a puncture device of a medical needle assembly, etc.).

Referring to the embodiment (implementation) as depicted in FIG. 3, for instance, in accordance with a third option, the signal-liberating feature 105 (of the elongated medical tubular assembly 102) may entirely include signal-enhancing material with no signal-blocking material; this arrangement may allow for improved signal communication between the signal-transceiving device 900 (also called surface electrodes or electrode which can transmit or receive electrical signal) and the signal-transmitting device 800 (such as a puncture device of a medical needle assembly, etc.).

Referring to the embodiment (implementation) as depicted in FIG. 3, for instance, in accordance with a fourth option, the elongated medical tubular assembly 102 may include (referring to FIG. 7) at least one device (such as distal electrode) mounted to a portion (such as the distal tip 104) of the elongated medical tubular assembly 102.

Referring to the embodiment (implementation) as depicted in FIG. 3, by utilizing the elongated medical tubular assembly 102, the signal-transmitting device 800 may be advantageously less likely to disappear from a medical image (also called a medical map, to be generated by the medical-imaging system 902) when the signal-transmitting device 800 is moved along the interior portion or section of the elongated medical tubular assembly 102. In this manner, the signal-transmitting device 800 may become advantageously visible to the medical-imaging system 902 when the signal-transmitting device 800 is moved along the interior of the elongated medical tubular assembly 102. The elongated medical tubular assembly 102 may improve the visualization of the signal-transmitting device 800 during a medical procedure, such as the transseptal puncture, etc.

Referring to the embodiment (implementation) as depicted in FIG. 3, for the case where a radiofrequency-emitting medical needle and a transseptal sheath and a transseptal dilator are required, the elongated medical tubular assembly 102 may include the transseptal dilator, (it will be appreciated that the system may include a sheath, a dilator and a puncture device, and the signal liberating feature 105 may be positioned or made in the dilator), and may have any one or more of the following technical features: (a) any usable length (such as, about 67 centimeters, 85 centimeters, etc.); (b) an internal diameter (such as, about 0.032 inches, etc.) configured to accommodate a guidewire assembly, a radiofrequency emitting needle; (c) an outer diameter (such as, about 8 French, about 8.5 French, etc.) configured to fit into a sheath assembly; (d) a perforated distal tip section of the elongated medical tubular assembly 102; (e) at least one distal device (such as electrode) positioned on the distal tip section of the elongated medical tubular assembly 102; (f) a shaft made of high-density polyethylene (HDPE); and/or (g) a luer-type connection made of high-density polyethylene.

Referring to the embodiment (implementation) as depicted in FIG. 3, for the case where a radiofrequency-emitting medical needle and a transseptal sheath and a transseptal dilator are required, the elongated medical tubular assembly 102 may include the transseptal dilator, and may have: (a) any usable (desirable) length (such as, about 67 centimeters, about 85 centimeters, etc.) and/or curves (such as, a D0-type curve, a D1-type curve, etc.), (b) an inner diameter (such as, about 0.035 inches) configured to accommodate the radiofrequency-emitting medical wire; (b) have an outer diameter (such as, about 8.5 French) configured to fit into the transseptal sheath; (d) a perforated tip section; (e) at least one distal device (electrode) mounted to a distal tip section; (f) a shaft made of a high-density polyethylene and a metal tube (hypotube) that terminates before the tip section; (g) a radiopaque and/or echogenic material (such as, have a platinum band, an iridium band, a coil, etc.); and/or (h) a hub made of polycarbonate.

Referring to the embodiment (implementation) as depicted in FIG. 3, for the case where the elongated medical tubular assembly 102 is configured to include a steerable sheath (known and not depicted), the elongated medical tubular assembly 102 may be made of a combination of low-density polyethylene (LDPE) and a high-density polyethylene (HDPE). The LDPE may be positioned at the distal region (of the elongated medical tubular assembly 102), and the HDPE may be positioned at the proximal region (of the elongated medical tubular assembly 102) to improve and/or facilitate steerability.

Referring to the embodiment (implementation) as depicted in FIG. 4, the signal-transmitting device 800 has been extended into (retracted within) the interior of the elongated medical tubular assembly 102 to such an extent that the signal-transceiving device 900 is still able to reliably detect the presence of the signal-transmitting device 800, and generate a medical image thereof (of the elongated medical tubular assembly 102) with help or assistance from the signal-liberating feature 105 of the elongated medical tubular assembly 102. For instance, the spaced-apart signal-transceivers (901A, 901B, 901C), are able to successfully triangulate a reliable signal emanating from the signal-transmitting device 800 (since the signal-liberating feature 105, or the spaced-apart perforations (106A, 106B, 106C), help facilitate said signal communication). In sharp contrast to FIG. 2, the spaced-apart signal-transceivers (901A, 901B, 901C), as depicted in FIG. 4, are able to reliably determine the location of a signal. Successful triangulation requires all of the spaced-apart signal-transceivers (901A, 901B, 901C) to receive an incoming signal from (transmitted from) the signal-transmitting device 800, as a result of the presence of the signal-liberating feature 105. Successful triangulation results when a quantity of three spaced-apart signal-transceivers (901A, 901B, 901C), in use, adequately receive any incoming signal from the signal-transmitting device 800 (with the presence of the signal-liberating feature 105). For this case, the medical-imaging system 902 is able to provide an adequate visual display of the medical image of the location (such as the movements) of the signal-transmitting device 800 while the signal-transmitting device 800 remains, at least in part, within the lumen 108 (of the elongated medical tubular assembly 102) and/or positioned rearward from the distal tip 104 (of the elongated medical tubular assembly 102). It will be appreciated that this case mitigates, at least in part, inadvertent injury to the patient 700 since the signal-liberating feature 105, or the spaced-apart perforations (106A, 106B, 106C), assist (in use) with (facilitate) signal communication from the signal-transmitting device 800 to the spaced-apart signal-transceivers (901A, 901B, 901C) of the medical-imaging system 902. For this case, the physician is not operating blindly (as is the case depicted in FIG. 2). The signal-liberating feature 105 (of the elongated medical tubular assembly 102) helps the spaced-apart signal-transceivers (901A, 901B, 901C) to successfully triangulate the location of the signal-transmitting device 800, thereby allowing the medical-imaging system 902 to provide a visual display of the medical image for the signal-transmitting device 800.

Figure 5:
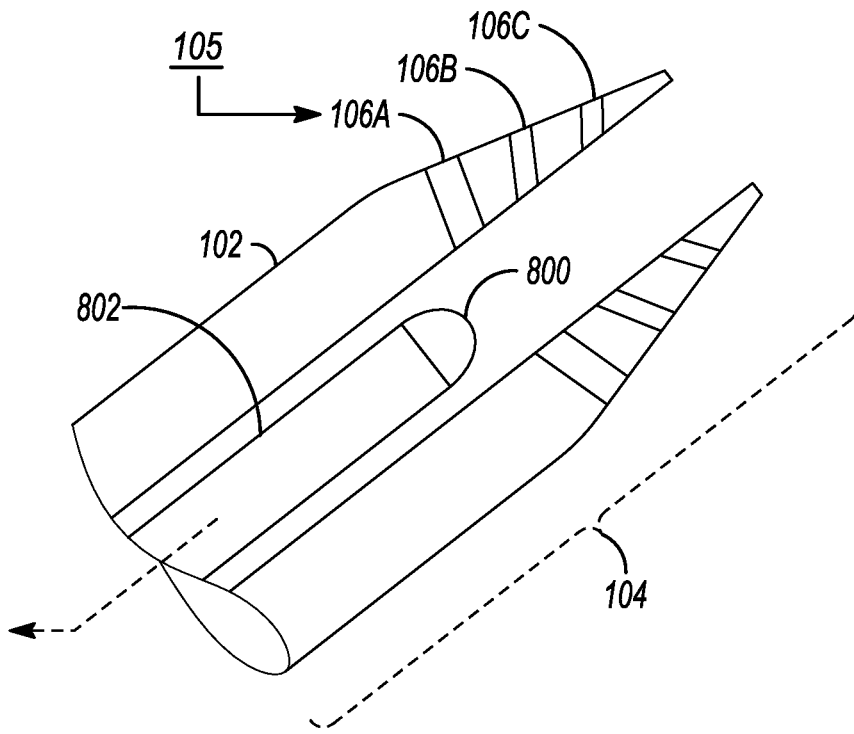
FIG. 5 and FIG. 6 depict a cross-sectional view (FIG. 5) of an embodiment (implementation) of the elongated medical tubular assembly of FIG. 1, and a schematic view (FIG. 6) of a display unit of a medical-imaging system depicting an image of the elongated medical tubular assembly of FIG. 5.
Figure 6:
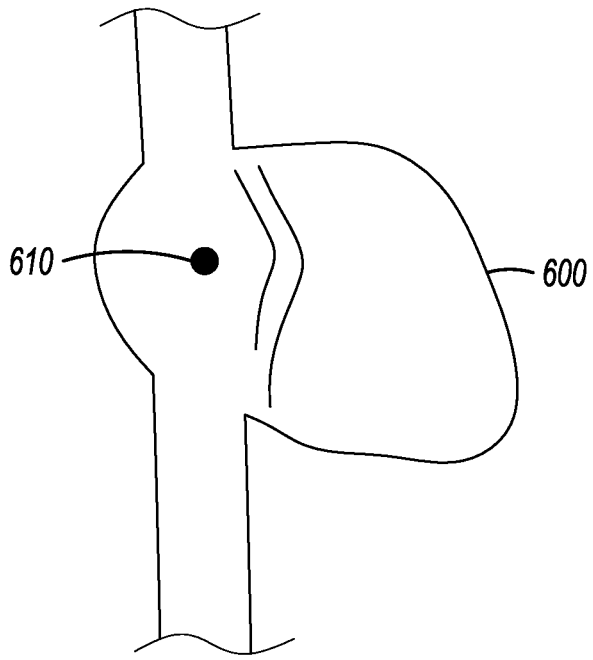

FIG. 5 and FIG. 6 depict a cross-sectional view (FIG. 5) of an embodiment (implementation) of the elongated medical tubular assembly 102 of FIG. 1, and a schematic view (FIG. 6) of a display unit of a medical-imaging system 902 depicting an image of the elongated medical tubular assembly 102 of FIG. 5.

Referring to the embodiment (implementation) as depicted in FIG. 5, the signal-transmitting device 800 is positioned (located) within the elongated medical tubular assembly 102. The signal-transmitting device 800 is positioned proximate to the signal-liberating feature 105, or the spaced-apart perforations (106A, 106B, 106C), at a location that is beyond the influence of the signal-liberating feature 105. For this case, the signal-liberating feature 105 is unable to assist in signal communication between the signal-transmitting device 800 and the signal-transceiving device 900 (or the spaced-apart signal-transceivers (901A, 901B, 901C) of the medical-imaging system 902, as depicted in FIG. 3). For this case, the signal-transceiving device 900 is not able to receive any suitable signal communication from the signal-transmitting device 800 without help (assistance) from the signal-liberating feature 105.

Referring to the embodiment (implementation) as depicted in FIG. 6, a medical image 600 (such as, the three-dimensional map of the heart of the patient 700 of FIG. 3) is generated by the medical-imaging system 902 (of FIG. 3). A medical image 610 of the signal-transmitting device 800 may or may not be able to be reliably detected by the signal-transceiving device 900 of the medical-imaging system 902 (depending on the location of the signal-transmitting device 800 within the elongated medical tubular assembly 102 relative to the signal-liberating feature 105). The medical image 610 is depicted in FIG. 6, merely to indicate that this might be the possible location of the signal-transmitting device 800 (if the devices of the signal-transceiving device 900 were, in fact, able to receive signal communication from the signal-transmitting device 800). It will be appreciated that for this case, position or location of the signal-transmitting device 800 relative to the elongated medical tubular assembly 102 is unknown (but is depicted for the sake of understanding). It is noted that the medical image 600 of the biological feature of the patient 700 is depicted in a tented condition (that is, the distal portion of the elongated medical tubular assembly 102 is pushing against a biological wall of the patient 700) even though the medical image of the signal-transmitting device 800 is not known or identified by the medical-imaging system 902. In summary, what may be desired is to provide a better arrangement for the case (as depicted in FIG. 6) so that the medical-imaging system 902 is able to provide (display) an adequate medical image that may be more meaningful (helpful), for the physician, than the case as depicted in FIG. 6.

Figure 7:
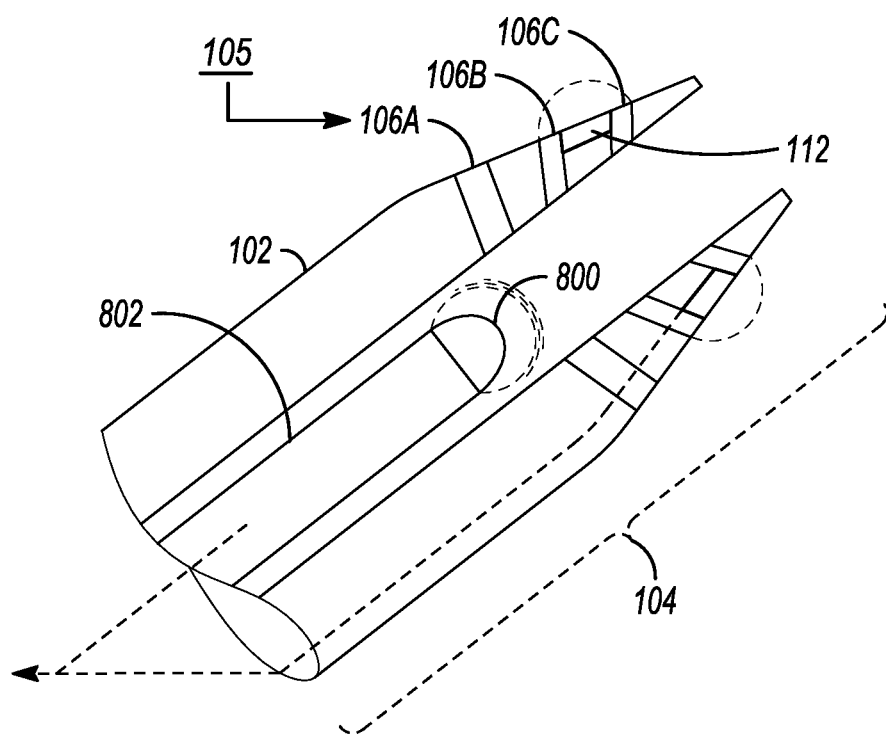
FIG. 7 and FIG. 8 depict a cross-sectional view (FIG. 7) of an embodiment (implementation) of the elongated medical tubular assembly of FIG. 1, and a schematic view (FIG. 8) of a display unit of a medical-imaging system depicting an image of the elongated medical tubular assembly of FIG. 7.
Figure 8:
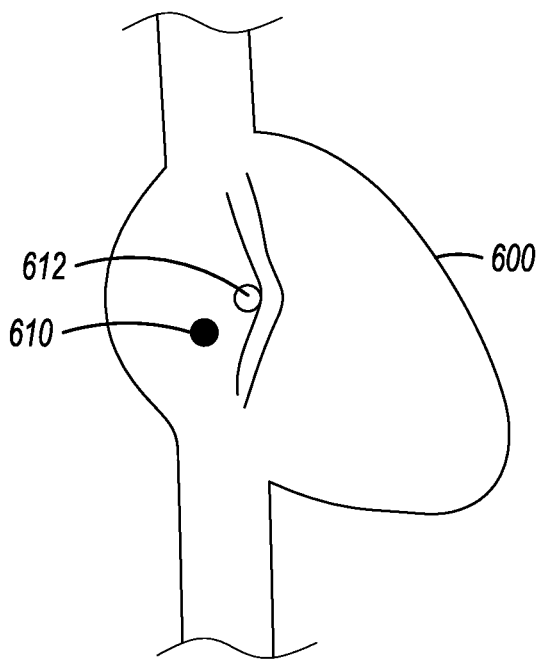

FIG. 7 and FIG. 8 depict a cross-sectional view (FIG. 7) of an embodiment (implementation) of the elongated medical tubular assembly 102 of FIG. 1, and a schematic view (FIG. 8) of a display unit of a medical-imaging system 902 depicting an image of the elongated medical tubular assembly 102 of FIG. 7.

Referring to the embodiment (implementation) as depicted in FIG. 7, there is depicted the output of the display system of the medical-imaging system 902. The elongated medical tubular assembly 102 includes a distal device 112 (such as electrode). The distal device 112 is located (mounted) at the distal tip 104. The distal device 112 is positioned on an outer surface of the elongated medical tubular assembly 102. The distal device 112 is located (mounted) at the distal tip 104 proximate to the exit portal of the lumen 108. The distal device 112 is spaced apart from the signal-liberating feature 105 or the spaced-apart perforations (106A, 106B, 106C). The distal device 112 is configured to selectively emit a signal to be transmitted to the signal-transceiving device 900 of the medical-imaging system 902 of FIG. 3. The distal device 112 mitigates, at least in part, the case depicted in FIG. 5 and FIG. 6 for the case where the signal-liberating feature 105 might be unable to assist in (influence) signal communication from the signal-transmitting device 800 to the signal-transceiving device 900 of FIG. 3; this arrangement permits the medical-imaging system 902 to provide an improved medical image (as depicted in FIG. 8). In summary, the distal device 112 is positioned proximate to the distal tip 104. The distal electrode 112 is configured to provide information (such as, the spatial position of the distal tip 104) to the medical-imaging system 902 (preferably via the signal-transceiving device 900).

Referring to the embodiment (implementation) as depicted in FIG. 8, there is depicted the output of the display system of the medical-imaging system 902 of FIG. 3 for the case where the distal device 112 (as depicted in FIG. 7) is utilized. The medical image 612 is associated with the distal device 112. The medical image 610 of the signal-transmitting device 800 may or may not be visible on the display system of the medical-imaging system 902 (depending, of course, on the location of the signal-transmitting device 800 relative to the signal-liberating feature 105). It will be appreciated that, as depicted in FIG. 8, the relative position between the signal-transmitting device 800 to the signal-liberating feature 105 is such that the signal-liberating feature 105 is able to permit signal communication between the signal-transmitting device 800 and the medical-imaging system 902, and therefore the medical image 610 is depicted for this case.

Figures 9, 10:
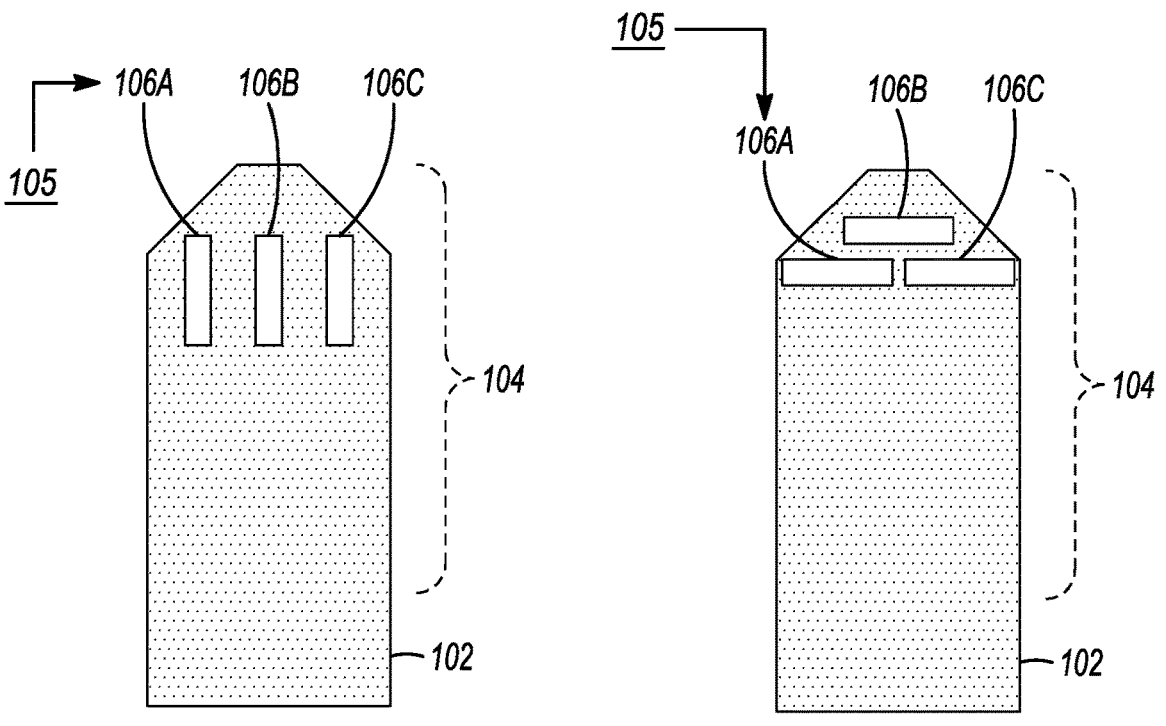
FIG. 9, FIG. 10 and FIG. 11 depict side views of the elongated medical tubular assembly of FIG. 1.
Figure 11:
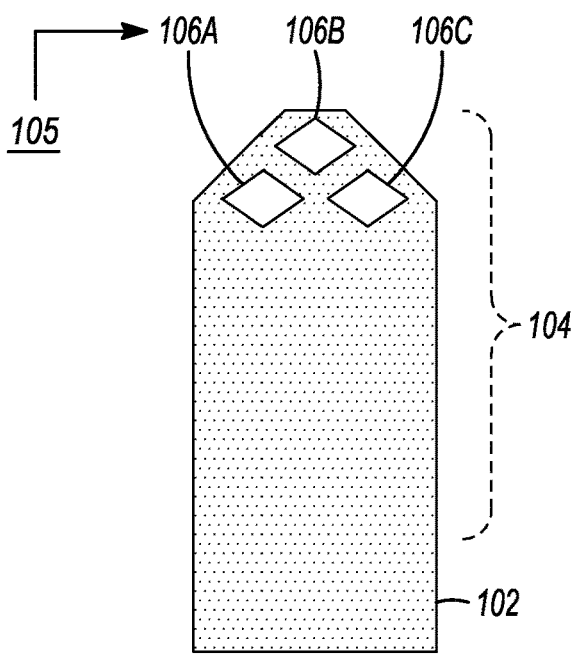

FIG. 9, FIG. 10 and FIG. 11 depict side views of the elongated medical tubular assembly 102 of FIG. 1.

Referring to the embodiment (implementation) as depicted in FIG. 9, the spaced-apart perforations (106A, 106B, 106C) include spaced-apart rectangular slits aligned along the longitudinal axis of the elongated medical tubular assembly 102, and are positioned equidistant from the exit portal of the elongated medical tubular assembly 102.

Referring to the embodiment (implementation) as depicted in FIG. 10, the spaced-apart perforations (106A, 106B, 106C) include spaced-apart rectangular slits aligned along the radial axis of the elongated medical tubular assembly 102.

Referring to the embodiment (implementation) as depicted in FIG. 11, the spaced-apart perforations (106A, 106B, 106C) include spaced-apart diamond-shaped openings aligned along the radial axis of the elongated medical tubular assembly 102.

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the disclosure which does not materially modify the disclosure. Similarly, unless specifically made clear from its context, numerical values should be construed to include certain tolerances that the person skilled in the art would recognize as having negligible importance as they do not materially change the operability of the disclosure. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options may be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the disclosure. The foregoing has outlined the non-limiting embodiments (examples). The description is made for particular non-limiting embodiments (examples). It is understood that the non-limiting embodiments are merely illustrative as examples.

What is claimed is:

1. An apparatus for use with a patient, a signal-transmitting device and a signal-transceiving device of a medical-imaging system, the apparatus comprising:

an elongated medical tubular assembly having a distal tip configured to be received, at least in part, in the patient; and the elongated medical tubular assembly being configured to receive, at least in part, the signal-transmitting device at the distal tip; and the distal tip comprising a signal-liberating feature that includes spaced-apart perforations configured to improve, at least in part, transmission of a signal from the signal-transmitting device toward the signal-transceiving device of the medical-imaging system.

2. An apparatus for use with a patient, having a signal-transmitting device and a signal-transceiving device of a medical-imaging system, the apparatus comprising:

an elongated medical tubular assembly configured to be received, at least in part, in the patient; and the elongated medical tubular assembly having a distal tip that comprises a signal-liberating feature that includes spaced-apart perforations and is configured to improve, at least in part, transmission of a signal from the signal-transmitting device, positioned in an interior of the elongated medical tubular assembly, toward the signal-transceiving device of the medical-imaging system.

3. The apparatus of claim 2, wherein the distal tip is configured to be received, at least in part, in the patient.

4. The apparatus of claim 2, wherein:

the elongated medical tubular assembly defines a lumen extending from the distal tip toward a proximal end of the elongated medical tubular assembly; and the lumen is configured to receive, at least in part, the signal-transmitting device in such a way that the lumen, in use, receives, at least in part, the signal-transmitting device at the signal-liberating feature.

5. The apparatus of claim 2, wherein the elongated medical tubular assembly includes a distal electrode configured to provide information to the medical-imaging system.

6. The apparatus of claim 2, further comprising:

a distal device being positioned proximate to the distal tip of the elongated medical tubular assembly; and the distal device being configured to provide information to the medical-imaging system.

7. The apparatus of claim 2, wherein the signal-transmitting device is installed to an elongated medical needle.

8. The apparatus of claim 2, wherein the signal-transmitting device includes an energy emitter configured to selectively emit energy.

9. The apparatus of claim 2, wherein the signal-transmitting device includes an energy emitter configured to selectively emit energy used for forming a puncture through, or cutting a portion of, a biological feature of the patient.

10. The apparatus of claim 2, wherein the elongated medical tubular assembly is an elongated medical needle with the signal-transmitting device mounted thereto.

11. The apparatus of claim 2, wherein the elongated medical tubular assembly includes a medical catheter assembly, a medical dilator assembly, or a medical sheath assembly.

12. The apparatus of claim 2, wherein:

the spaced-apart perforations extend from the interior of the elongated medical tubular assembly to an exterior of the elongated medical tubular assembly; and wherein the spaced-apart perforations are configured to provide fluid communication between the interior of the elongated medical tubular assembly and the exterior of the elongated medical tubular assembly.

13. The apparatus of claim 2, wherein the signal-liberating feature further includes a side wall body member configured to permit transmission of signal communication from the signal-transmitting device to the medical-imaging system.

14. The apparatus of claim 2, wherein the signal-liberating feature further includes a signal-enhancing material surrounded by signal-blocking material of the elongated medical tubular assembly.

15. The apparatus of claim 2, wherein the signal-liberating feature further includes a signal-enhancing material.

16. The apparatus of claim 2, wherein the spaced-apart perforations include spaced-apart rectangular slits aligned along a longitudinal axis of the elongated medical tubular assembly and positioned equidistant from an exit portal of the elongated medical tubular assembly.

17. The apparatus of claim 2, wherein the spaced-apart perforations include spaced-apart rectangular or diamond-shaped slits aligned along a radial axis of the elongated medical tubular assembly.

18. A method for enhancing transmission of a signal from a signal-transmitting device toward a signal-transceiving device of a medical-imaging system while the signal-transmitting device is positioned in a patient, the method comprising:

receiving, at least in part, a distal tip of an elongated medical tubular assembly into the patient, in which the distal tip comprises a signal-liberating feature that includes spaced-apart perforations, and in which the elongated medical tubular assembly defines a lumen extending from the distal tip toward a proximal end of the elongated medical tubular assembly, and in which the lumen is configured to receive, at least in part, the signal-transmitting device in such a way that the lumen, in use, receives, at least in part, the signal-transmitting device at the spaced-apart perforations defined by the distal tip; and using, at least in part, the spaced-apart perforations to improve, at least in part, transmission of the signal from the signal-transmitting device, positioned in the lumen, toward the signal-transceiving device of the medical-imaging system.

* * * * *